United States Patent [19]
Delorme et al.

[11] Patent Number: 5,728,648
[45] Date of Patent: Mar. 17, 1998

[54] BIODEGRADABLE FERTILIZER AND PEST CONTROL COMPOSITION COMPRISING LIMONENE

[76] Inventors: Virgil A. Delorme, 23615 1/2 Hillview Rd., San Bernardino, Calif. 92404; Thomas Crisofulli, 13066 Balboa La., Moreno Valley, Calif. 92553; Madelyn Joy Warner, 3908 Oakwood Pl., Riverside, Calif. 92506

[21] Appl. No.: 715,072

[22] Filed: Sep. 19, 1996

[51] Int. Cl.$^6$ ............................................. A01N 27/00
[52] U.S. Cl. ................................... 504/101; 514/763
[58] Field of Search ..................... 504/101; 71/DIG. 1; 514/763

[56] References Cited

U.S. PATENT DOCUMENTS

| | | | |
|---|---|---|---|
| 4,379,168 | 4/1983 | Dotolo | 424/356 |
| 4,911,952 | 3/1990 | Doane et al. | 427/213.31 |
| 5,264,019 | 11/1993 | Gossett, Jr. et al. | 71/64.07 |
| 5,543,435 | 8/1996 | Chastain et al. | 514/729 |

*Primary Examiner*—S. Mark Clardy
*Attorney, Agent, or Firm*—Michael I. Kroll

[57] ABSTRACT

The present invention relates to an improved fertilizing composition of the type containing nitrogen, phosphorus and potassium, with the improvement being the addition of 1-methyl-4-(1-methylethenyl)cyclohexene (i.e., limonene) as an insecticide and fungicide.

5 Claims, 1 Drawing Sheet

BIODEGRADABLE FERTILIZER AND PEST CONTROL COMPOSITION COMPRISING LIMONENE

BACKGROUND OF THE INVENTION

1. Field of the Invention

The present invention relates to the field of fertilizers and pest control compositions. More specifically, the present invention is concerned with a single composition which is effective as a fertilizer, insecticide and fungicide in the cultivation of land. Even more specifically, the present invention is concerned with the use of 1-methyl-4-(1-methylethenyl)cyclohexene as a pest control and fungicidal additive to conventional fertilizers in agricultural use.

2. Description of the Prior Art

Virtually all commercial fertilizers contain, as the major fertilizing substances, nitrogen, phosphorous and potassium. These primary elemental nutrients are provided for in various forms and relative amounts. For example, nitrogen is commonly provided in urea and/or ammonium nitrate, phosphorous in phosphonic acid and potassium in potassium hydroxide (potash).

Fertilizers also commonly contain secondary nutrients such as calcium, magnesium and sulfer. Common sources for these are lime, dolomite and sulfates, respectively.

Trace nutrients often found in fertilizing compositions include iron, zinc, manganese, copper, boron, molybdenum. Trace minerals are often provided in chelated form, for example, with EDTA (ethylenediaminetetraacetic acid). Typical examples include EDTA copper, EDTA iron, EDTA manganese and EDTA zinc. Boron is most often provided as boric acid, while molybdenum is commonly provided as sodium molybdate.

It should be noted that fertilizers which contain only nutrients such as those described above are not useful for controlling pests, such as insects, or as fungicides. It is common, when insecticidal or fungicidal activity is required, to add an insecticide or fungicide in a separate step. Accordingly, it would be a significant advantage to have a single formulation which is effective as 1) a fertilizer, 2) an insecticide, and 3) a fungicide.

SUMMARY OF THE INVENTION

The present invention is concerned with a single composition which is effective as a fertilizer, an insecticide and a fungicide. The inventive composition contains sources of nitrogen, phosphorous and potassium as primary elemental nutrients and further includes a functional amount of 1-methyl-4-(1-methylethenyl)cyclohexene as a pesticide and fungicide.

An object of the present invention is therefore a single composition which is effective as a fertilizer, an insecticide and a fungicide.

A further objective of the invention is a fertilizing, insecticidal and fungicidal composition produced entirely from organic components.

Another objective of the invention is a fertilizing, insecticidal and fungicidal composition which is biodegradable.

Yet another objective of the invention is a fertilizing, insecticidal and fungicidal composition which is safe to use.

A still further objective of the invention is a fertilizing, insecticidal and fungicidal composition which is easy to apply with a single application.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawing.

LIST OF REFERENCE NUMERALS UTILIZED IN THE DRAWING

Figure 1:
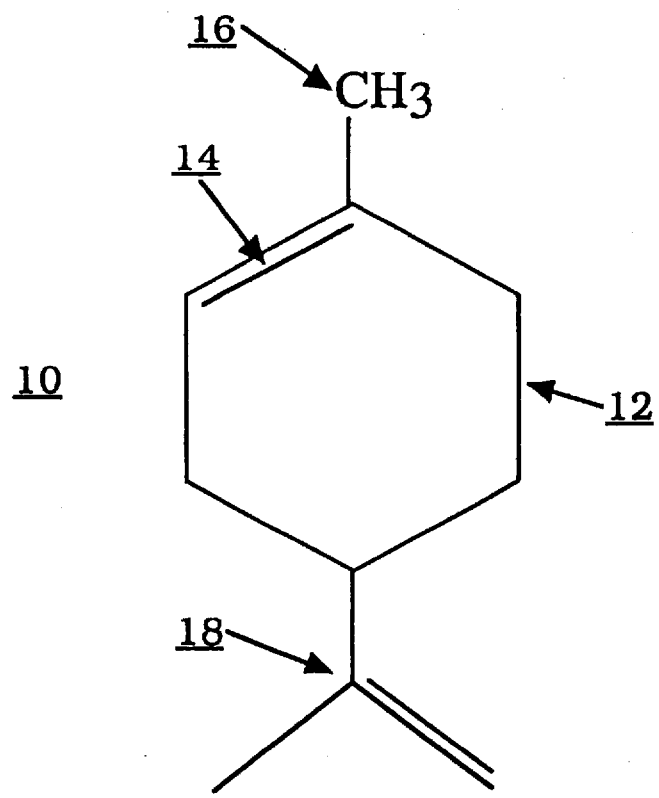
FIG. 1 is a chemical diagram of the insecticidal and fungicidal component of the present invention, 1-methyl-4-(1-methylethenyl)cyclohexene.

10—The chemical structure for 1-methyl-4-(1-methylethenyl)cyclohexene.

12—The central portion of the 1-methyl-4-(1-methylethenyl)cyclohexene molecule (10), a cyclohexene ring (12).

14—The double bond (14) in the cyclohexene ring (12), between carbon atoms 1 and 2.

16—The methyl moiety at the 1-position of the cyclohexene ring (12).

18—The 1-methylethenyl moiety at the 4-position of the cyclohexene ring (12).

DETAILED DESCRIPTION OF THE PREFERRED EMBODIMENT

As discussed above, the fungicidal and insecticidal component in the present invention is 1-methyl-4-(1-methylethenyl)cyclohexene. This compound is also known formally as (R)-4-isopropenyl-1-methylcyclohexene and informally as citrene or d-limonene. Its chemical formula is $C_{10}H_{16}$ and it has a molecular weight of 136.2. It is normally an oil with a boiling point of 168° C. It is a terpene derived from citrus, usually orange or lemon, rinds, and is commonly used in perfumes and flavors.

The present invention concerns a the surprising discovery that 1-methyl-4-(1-methylethenyl)cyclohexene is not only effective both as an insecticide and a fungicide, but that it is also compatible with commercial fertilizing compositions, thus enabling, for the first time, a single composition effective as a fertilizer, an insecticide and a fungicide.

In its simplest form, the present invention consists of a standard fertilizing composition comprising sources of nitrogen, phosphorous and potassium, in combination with an insecticidally and fungicidally functional amount of 1-methyl-4-(1-methylethenyl)cyclohexene.

In practice, the concentration of 1-methyl-4-(1-methylethenyl)cyclohexene will generally be from about 0.1 to about 10.0 weight percent of the total composition.

Preferably, the concentration of 1-methyl-4-(1-methylethenyl)cyclohexene will be from about 1.0 to about 5.0 weight percent of the total composition.

Most preferably, the concentration of 1-methyl-4-(1-methylethenyl)cyclohexene will be about 3.0 weight percent of the total composition.

It will be understood that each of the elements described above, or two or more together, may also find a useful application in other types of applications differing from the type described above.

While the invention has been illustrated and described as embodied in a fertilizing, fungicidal and insecticidal composition, it is not intended to be limited to the details shown, since it will be understood that various omissions, modifications, substitutions and changes in the forms and details of the formulation illustrated and in its operation can be made by those skilled in the art without departing in any way from the spirit of the present invention.

Without further analysis, the foregoing will so fully reveal the gist of the present invention that others can, by applying current knowledge, readily adapt it for various application without omitting features that, from the standpoint of prior art, fairly constitute essential characteristics of this invention.

What is claimed as new and desired to be protected by Letters Patent is set forth in the appended claims:

1. An improved fertilizing composition of the type containing nitrogen, phosphorous and potassium, wherein the improvement comprises the addition of 1-methyl-4-(methylethenyl)cyclohexene in an amount which is active in said composition as both an insecticide and fungicide.

2. A composition as defined in claim 1, wherein said 1-methyl-4-(1-methylethenyl)cyclohexene comprises from about 1.0 to about 5.0 weight percent of the total composition.

3. A composition as defined in claim 2, wherein said 1-methyl-4-(1-methylethenyl)cyclohexene comprises about 3.0 weight percent of the total composition.

4. A method of making and using an antifungal, insecticidal fertilizing composition from a fertilizing composition comprising adding to said fertilizing composition a functional amount of 1-methyl-4-(1-methylethenyl)cyclohexene in a form which is effective as an insecticide and a fungicide and employing said composition as a fertilizer, an insecticide and a fungicide and applying said composition to a locus in need of fertilization and both insecticidal and fungicial treatment.

5. A method of making and using an antifungal fertilizing composition from a fertilizing composition comprising adding to a fertilizing composition a functional amount of 1-methyl-4-(1-methylethenyl)-cyclohexene in a form which is effective as a fungicide and employing said composition as a fertilizer and a fungicide and applying said composition to a locus in need of fertilization and fungicial treatment.

* * * * *